US009890116B2

(12) United States Patent
Anelli et al.

(10) Patent No.: US 9,890,116 B2
(45) Date of Patent: Feb. 13, 2018

(54) PROCESS FOR THE PREPARATION OF A SULFATED DERIVATIVE OF 3,5-DIIODO-O-[3-IODOPHENYL]-L-TYROSINE

(75) Inventors: Pier Lucio Anelli, Milan (IT); Maria Argese, Sedriano (IT); Luciano Lattuada, Bussero (IT); Sonia Gazzetto, Cascinette d'Ivrea (IT); Laura Galimberti, Fara Gera d'Adda (IT); Valeria Boi, Strambino (IT); Livio Cavalieri, Milan (IT); Fulvia Vella, Monza (IT)

(73) Assignee: BRACCO IMAGING S.p.A., Milan (IT)

( * ) Notice: Subject to any disclaimer, the term of this patent is extended or adjusted under 35 U.S.C. 154(b) by 370 days.

(21) Appl. No.: 14/110,237

(22) PCT Filed: Apr. 5, 2012

(86) PCT No.: PCT/EP2012/056274
§ 371 (c)(1),
(2), (4) Date: Oct. 7, 2013

(87) PCT Pub. No.: WO2012/136761
PCT Pub. Date: Oct. 11, 2012

(65) Prior Publication Data
US 2014/0024717 A1 Jan. 23, 2014

Related U.S. Application Data

(63) Continuation-in-part of application No. 13/083,047, filed on Apr. 8, 2011, now abandoned.

(30) Foreign Application Priority Data

Apr. 29, 2011 (IT) .................... MI2011A0713

(51) Int. Cl.
*C07C 303/24* (2006.01)
*A61K 9/20* (2006.01)
*A61K 31/198* (2006.01)
*C07D 495/04* (2006.01)
*C07C 227/16* (2006.01)
*C07F 1/04* (2006.01)

(52) U.S. Cl.
CPC .......... *C07C 303/24* (2013.01); *A61K 9/2054* (2013.01); *A61K 31/198* (2013.01); *C07C 227/16* (2013.01); *C07D 495/04* (2013.01); *C07F 1/04* (2013.01)

(58) Field of Classification Search
CPC ... C07C 227/16; C07C 303/24; C07C 229/36; C07C 305/24; C07D 495/04; C07F 1/04; A61K 31/198; A61K 9/2054
See application file for complete search history.

(56) References Cited

U.S. PATENT DOCUMENTS

| 2,970,165 | A | 1/1961 | Raymond et al. |
| 2,993,928 | A | 7/1961 | Razdan et al. |
| 3,313,838 | A * | 4/1967 | Rozzi .................... C07C 309/00 422/205 |
| 3,313,839 | A | 4/1967 | Rozzi |
| 4,254,095 | A | 3/1981 | Fisher et al. |
| 5,116,828 | A | 5/1992 | Miura et al. |
| 5,158,978 | A | 10/1992 | Rubin |
| 5,225,204 | A | 7/1993 | Chen et al. |
| 5,272,078 | A | 12/1993 | Larsen et al. |
| 5,324,522 | A | 6/1994 | Krenning et al. |
| 5,385,897 | A * | 1/1995 | Teutsch ................ C07D 513/04 514/210.05 |
| 5,753,254 | A | 5/1998 | Khan et al. |
| 5,955,105 | A | 9/1999 | Mitra et al. |
| 5,958,979 | A | 9/1999 | Lahr et al. |
| 6,056,975 | A | 5/2000 | Mitra et al. |
| 6,406,667 | B1 | 6/2002 | Singh et al. |
| 6,555,581 | B1 | 4/2003 | Franz et al. |
| 6,599,942 | B1 | 7/2003 | Kukkola |
| 6,646,007 | B1 | 11/2003 | Schreder et al. |
| 6,740,680 | B1 | 5/2004 | Danforth, Jr. et al. |
| 6,855,333 | B1 | 2/2005 | Spireas |

(Continued)

FOREIGN PATENT DOCUMENTS

CA 2333193 A1 11/1999
CA 2523079 A1 11/2004

(Continued)

OTHER PUBLICATIONS

IT 1981997 Google Translation of Example 9, pp. 36-37.*
Chlorosulfonic acid MSDS (Sciencelab.com, created Oct. 11, 2005, updated May 21, 2013, p. 1-6).*
Office Action for Australian application No. 2012238665, dated Feb. 22, 2016.
Office Action for European application No. 12712124.2, dated Dec. 8, 2015.
Office Action for Russian application No. 2013149419, dated Jan. 11, 2016 (English translation).
Office Action for Israel application No. 228757, dated Oct. 14, 2015 (English translation).
Application, National Phase of PCT/EP2003/12584 (WO2004/043452), U.S. Appl. No. 10/532,447, filed Apr. 22, 2005, now US-2005-0272816-A1, publication date, Aug. 12, 2005.

(Continued)

Primary Examiner — Kortney L. Klinkel
(74) Attorney, Agent, or Firm — Vivicar Law, PLLC

(57) ABSTRACT

The present invention relates to a process for the preparation of the mono sodium salt of the derivative 3,5-diiodo-O-[3-iodo-4-(sulphooxy)phenyl]-L-tyrosine (T3S) by starting from the corresponding phenolic compound, in the presence of chloro-sulfonic acid and dimethylacetamide as a solvent. The so obtained T3S compound may conveniently be isolated in a pure form as a solid in good yields. The present invention further relates to the process for T3S preparation, wherein the starting reagent is T2 and further comprising the formulation of such compound in tablets. Furthermore, the invention discloses non-radioactive immunoassays based on T3S derivatives.

20 Claims, 2 Drawing Sheets

(56) References Cited

U.S. PATENT DOCUMENTS

| | | | |
|---|---|---|---|
| 6,979,462 | B1 | 12/2005 | Spireas |
| 7,052,717 | B2 | 5/2006 | Hanshew et al. |
| 7,067,148 | B2 | 6/2006 | Franz et al. |
| 7,101,569 | B2 | 9/2006 | Franz et al. |
| 7,163,918 | B2 | 1/2007 | Piccariello et al. |
| 7,691,411 | B2 | 4/2010 | Di Martino et al. |
| 7,723,390 | B2 | 5/2010 | Garavani et al. |
| 8,008,349 | B2 | 8/2011 | Schreder et al. |
| 2001/0051657 | A1 | 12/2001 | Chiang |
| 2002/0076827 | A1 | 6/2002 | Salhanick |
| 2003/0050344 | A1 | 3/2003 | Garavani et al. |
| 2003/0198668 | A1 | 10/2003 | Franz et al. |
| 2004/0063611 | A1 | 4/2004 | Schreder et al. |
| 2004/0156893 | A1 | 8/2004 | Klein et al. |
| 2005/0249801 | A1 | 11/2005 | Spireas |
| 2005/0266570 | A1 | 12/2005 | Carey et al. |
| 2005/0272816 | A1 | 12/2005 | Pinchera et al. |
| 2007/0014851 | A1 | 1/2007 | Burghart et al. |
| 2007/0049620 | A1* | 3/2007 | Kimura .............. A61K 31/437 514/332 |
| 2007/0276042 | A1 | 11/2007 | Gant et al. |
| 2008/0003284 | A1 | 1/2008 | Franz et al. |
| 2008/0193527 | A1 | 8/2008 | Ruiz Amenos et al. |
| 2010/0136109 | A1 | 6/2010 | Ross et al. |
| 2011/0064773 | A1 | 3/2011 | Leverve et al. |
| 2011/0245342 | A1 | 10/2011 | Pinchera et al. |

FOREIGN PATENT DOCUMENTS

| | | | |
|---|---|---|---|
| CN | 1711079 A | 12/2005 | |
| DE | 19541128 A1 | 4/1997 | |
| EP | 0550108 A1 | 7/1993 | |
| EP | 0466909 B1 | 6/1995 | |
| EP | 0732920 B1 | 10/2003 | |
| EP | 1291021 A2 | 12/2003 | |
| EP | 1433478 A1 | 6/2004 | |
| EP | 1560575 B1 | 9/2006 | |
| EP | 1322294 B1 | 12/2007 | |
| IT | 1981997 | 3/2000 | |
| IT | 1981997 A1 * | 3/2000 | |
| JP | 63-079824 A | 4/1988 | |
| JP | 5-255081 A | 10/1993 | |
| JP | 7-116031 A | 12/1995 | |
| WO | 91/11181 A1 | 8/1991 | |
| WO | 95/20953 A1 | 8/1995 | |
| WO | 97/17951 A2 | 5/1997 | |
| WO | 03/007994 A2 | 1/2003 | |
| WO | 02/28364 A2 | 4/2004 | |
| WO | 2004-043452 A1 | 5/2004 | |
| WO | 04/071432 A2 | 8/2004 | |
| WO | 05/004849 A2 | 1/2005 | |
| WO | 08/129303 A2 | 10/2008 | |
| WO | 08/138995 A1 | 11/2008 | |
| WO | 2008/140459 A1 | 11/2008 | |
| WO | WO 2009/123580 * | 10/2009 | .............. A61K 9/00 |

OTHER PUBLICATIONS

U.S. Appl. No. 13/083,047, Continuation-in-Part of U.S. Appl. No. 10/532,447, filed Apr. 8, 2011, now US-2011-0245342-A1, publication dated Oct. 6, 2011.

U.S. Appl. No. 13/755,279, Divisional of U.S. Appl. No. 13/083,047, filed Jan. 31, 2013, now US-2013-0146502A1, publication date Jun. 13, 2013.

U.S. Appl. No. 13/916,710, Divisional of U.S. Appl. No. 13/083,047, filed Jun. 13, 2013, now US-2013-0281536-A1, publication date Oct. 24, 2013.

Office Action for U.S. Appl. No. 13/755,279, dated Dec. 4, 2013, total: 21 pp.

Office Action for U.S. Appl. No. 10/532,447, dated May 14, 2014, total: 28 pp.

Office Action: Reexamination Decision for Chinese application No. 200810135762.7, dated Jan. 26, 2015 (English translation).

Office Action for Chinese application No. 201280023319.5, dated Sep. 9, 2015 (English translation).

Office Action: Final for U.S. Appl. No. 13/755,279, dated Jul. 31, 2014.

Office Action: Notice of Allowance for U.S. Appl. No. 13/755,279, dated Apr. 9, 2015.

Bunevicius R. et al., "Effects of Thyroxine as Compared with Thyroxine plus Triiodothyronine in Patients with Hypothyroidism", The New England Journal of Medicine, vol. 340(6), pp. 424-429, Feb. 11, 1999.

Chopra I. J. et al, "Demonstration of thyromimetic effects of 3,5,3'-triiodothyronine sulfate (T3S) in euthyroid rats" Thyroid 1996 United States, vol. 6, No. 3, 1996, pp. 229-232, XP009027310.

Feigenbaum, J. et al., "Simplified Method for the Preparation of Aromatic Sulfuric Acid Esters", Journal of the American Chemical Society, American Chemical Society, Washington DC, vol. 63, Jan. 1, 1941, pp. 3529-3530, XP002522192, ISSN: 0002-7863.

Herfindal, E. et al., Clinical Pharmmacy and Therapeutics: Fifth Edition, Williams & Wilkins, 1992.

LoPresti Jonathan S. et al: "Characteristics of 3,5,3'-Triiodothyronine Sulfate Metabolism in Euthyroid Man" Journal of Clinical Endocrinology and Metabolism, vol. 73(4), pp. 708-709, 1992.

Mol J. et al., "Synthesis and some properties of sulfate esters and sulfamates of iodothyronines", Endocrinology, vol. 117(1), pp. 1-7, Jul. 1985, NCBI Pub Med, www.pubmed.gov.

Mol J. et al., "Synthesis and some properties of sulfate esters and sulfamates of iodothyronines", Endocrinology, vol. 117, No. 1, 1985, pp. 1-7, XP009153115.

PCT International Search Report for PCT/EP03/12584, dated Mar. 25, 2004.

PCT International Preliminary Examination Report for PCT/EP03/12584, dated Feb. 24, 2005.

PCT International Search Report and Written Opinion for PCT/EP2012/056274, dated Jun. 14, 2012.

PCT International Search Report and Written Opinion for PCT/EP2012/056274, dated Aug. 8, 2012.

PCT Written Opinion of the International Preliminary Examining Authority for PCT/EP2012/056274, dated Mar. 12, 2013.

PCT Written Opinion of the International Preliminary Examining Authority for PCT/EP2012/056274, dated May 31, 2013.

PCT International Preliminary Report on Patentability for PCT/EP2012/056274, dated Aug. 27, 2013.

Rudnic, E. et al., "Oral Solid Dosage Forms", Remington: The Science and Practice of Pharmacy, Ch. 92, 19th ed., pp. 1615-1649, Mack Publishing Company, Easton, PA 18042, 1995.

Santini Ferruccio et al: "Thyromimetic effects of 3,5,3'-triiodothyronine sulfate in hypothyroid rats" Endocrinology, vol. 133, No. 1, 1993, pp. 105-110, XP002272821.

The Code of Federal Regulations (Title 21—Food and Drugs, vol. 3, Apr. 1, 2012, §184.1328 glyceryl behenate).

Wu, S-Y et al., "Thyroxine Sulfate Is a Major Thyroid Hormone Metabolite and a Potential Intermediate in the Monodeiodination Pathways in Fetal Sheet", vol. 131(4), Endocrinology, pp. 1751-1756, 1992.

AACE Thyroid Guidelines, "American Association of Clinical Endocrinologists Medical Guidelines for Clinical Practice for the Evaluation and Treatment of Hyperthyroidism and Hypothyroidism: AACE Thyroid Task Force", Endocrine Practice, vol. 8, No. 6, Nov.-Dec. 2002, pp. 457-469.

Biondi, Bernadette et al., "Combination Treatment with T4 and T3: Toward Personalized Replacement Therapy in Hypothyroidism?", J Clin. Endocrinol. Metab, Special Feature Clinical Review, 2012, vol. 97, No. 7, doi:10.1210/jc.2011-3399, The Endocrine Society, pp. 1-16.

Chalmers, J.R. et al., "The Synthesis of Thyroxine and Related Substances. Part V. A Synthesis of L-Thyroxine from L-Tyrosine", 1949, pp. 3424-3433, http://pubs.rsc.org|doi:10.1039/JR9490003244.

Chopra, Inder J., "Nature, Sources and Relative Biologic Significance of Circulating Thyroid Hormones", Braverman LE., Utiger RD (eds) The Normal Thyroid , Lippincott, Philadelphia USA, 1991, pp. 126-143.

(56) References Cited

OTHER PUBLICATIONS

Chopra, Inder J. et al., "A Radioammunoassay for Measurement of 3,5,3'-Triiodothyronine Sulfate: Studies in Thyroidal and Nonthyroidal Diseases, Pregnancy, and Neonatal Life", Journal of Clinical Endocrinology and Metabolism, 1992, vol. 75, No. 1, pp. 189-194, The Endocrine Society.
De Herder, WW et al., "Rapid and Bacteria-Dependent In Vitro Hydrolysis of Iodothyronine-Conjugates by Intestinal Contents of Humans and Rats", Medical Biology, vol. 64, 1986, pp. 31-35.
Escobar-Morreale, Hector F. et al., "Reivew: Treatment of Hypothyroidism with Combinations of Levothyroxine plus Liothyronine", The Journal of Clinical Endocrinology & Metabolism, 2005, vol. 90, No. 8, pp. 4946-4954, The Endocrine Society, doi: 10.1210/jc.2005-0184.
Faber, J., et al., "Urinary Excretion of Free and Conjugated 3',5'-Diiodothyronine and 3,3'-Diiodothyronine", Journal of Clinical Endocrinology and Metabolism, 1981, vol. 53, No. 3, pp. 587-593, The Endocrine Society.
Goodman & Gilman's "The Pharmacological Basis of Therapeutics", Ninth Edition, Chapter 1 Pharmacokinetics, McGraw-Hill, 1996, p. 5.
Goodman & Gilman's "The Pharmacological Basis of Therapeutics", Ninth Edition, Section XIII Hormones and Hormone Antagonists, McGraw-Hill, 1996, pp. 1394-1395.
Gullo, Damiano et al., "Levothyroxine Monotherapy Cannot Guarantee Euthyroidism in All Athyreotic Patients", PLOS One, 2011, vol. 6, Issue 8, e22552, www.plosone.org, pp. 1-7.
Harrison's Principles of Internal Medicine, 16th edition (Manual), 2005, McGraw-Hill Companies, Inc., p. 2112.
Hemmila, Ilkka et al., "Europium as a Label in Time-Resolved Immunofluorometric Assays", Analytical Biochemistry, 1984, vol. 137, pp. 335-343, Academic Press Inc.
Kung, Mei-Ping et al., "Desulfation of 3,5,3'-Triiodothyronine Sulfate by Microsomes from Human and Rat Tissues", Endocrinology, vol. 122, No. 4, 1988, pp. 1195-1200.
Martindale "The Complete Drug Reference", 36th Edition (Manual), 2009, the Pharmaceutical Press, pp. 2167, 2171-2172, 2174.
Mol, Jan A. et al., "Rapid and Selective Inner Ring Deiodination of Thyroxine Sulfate by Rat Liver Deiodinase", Endocrinology, vol. 117, No. 1, 1986, pp. 8-12.
"Orange Book: Approved Drug Products with Therapeutic Equivalence Evaluations: query on Levothyroxine", FDA U. S. Food & Drug Administration, p. 1-14, Orange Book data updated through May 2012; Patent and Generic Drug Product Data Last Updated Jul. 2, 2012.
"Orange Book: Approved Drug Products with Therapeutic Equivalence Evaluations: query on Liothyronine", FDA U.S. Food & Drug Administration, p. 1-3, Orange Book data updated through May 2012; Patent and Generic Drug Product Data Last Updated Jul. 2, 2012.
Otten, M.H. et al., "Sulfation Preceding Deiodination of Iodothyronines in Rat Hepatocytes", Science, vol. 221, 1983, pp. 81-83.
Roberts, Caroline G.P. et al., "Hypothroidism", Seminar, The Lancet, 2004, vol. 363, pp. 793-803.
Roche, Jean et al., "Hepatic sulphate conjugation of 3,5,3'-triiodo-L-thyronine and the presence of a sulphuric ester of this hormone in bile and plasma", 1959, vol. 33, pp. 461-469.
Rohm and Haas, "Amberlite™ XAD™ 1600N: Macroreticular Polymeric Adsorbent", Mar. 2005, total of 4 pages.
Rooda, Sebo Jan Eelkman et al., "Metabolism of Triiodothyronine in Rat Hepatocytes", Endocrinology, 1989, vol. 125, No. 4, pp. 2187-2197, The Endocrine Society.
Santini, Ferruccio et al., "A Study of Metabolism of Deaminated and Sulfoconjugated Iodothyronines by Rat Placental Iodothyronine 5-Monodeiodinase", Endocrinology, 1992, vol. 131, No. 4, pp. 1689-1694.
Santini, Ferruccio et al., "Metabolism of 3,5,3'-Triiodothyronine Sulfate by Tissues of the Fetal Rat: A Consideration of the Role of Desulfation of 3,5,3'-Triiodothyronine Sulfate as a Source of T3", Pediatric Research, 1992, vol. 31, No. 6, pp. 541-544.
Santini, F. et al., "A Study of the Serum 3,5,3'-Triiodothyronine Sulfate Concentration in Normal and Hypothyroid Fetuses at Various Gestational Stages", Journal of Clinical Endocrinology and Metabolism, 1993, vol. 76, No. 6, pp. 1583-1587.
Santini, Ferruccio et al., "Serum Iodothyronines in the Human Fetus and the Newborn: Evidence for an Important Role of Placenta in Fetal Thyroid Hormone Homeostasis", Journal of Clinical Endocrinology and Metabolism, 1999, vol. 84, No. 2, pp. 493-498.
Santini, Ferruccio et al., "Evidence for the role of the type III-iodothyronine deiodinase in the regulation of 3,5,3'-triiodothyronine content in the human central nervous system", European Journal of Endocrinology, 2001, vol. 144, pp. 577-583, ISSN 0804-4643.
Santini, Ferruccio et al., Steady-State Serum T3 Concentrations for 48 Hours Following the Oral Administration of a Single Dose of 3,5,3'-Triiodothyronine Sulfate (T3S), Endocrine Practice, 2014, vol. 20, No. 7, pp. 680-689.
Spaulding, Stephen W. et al., "Studies on the Biological Activity of Triiodothyronine Sulfate", Journal of Clinical Endocrinology and Metabolism, vol. 74, No. 5, 1992, pp. 1062-1067.
The Merck Manual of Diagnosis and Therapy, 17th Edition, (Manual), 1999, pp. 92-95.
Visser, Theo J., "Role of sulfation in thyroid hormone metabolism", Chemico-Biological Interactions, vol. 92, 1994, pp. 293-303, Elsevier Science Ltd.
Wiersinga, Wilmar M., "Thyroid Hormone Replacement Therapy", Hormone Research, 2001, vol. 56(Suppl 1), pp. 74-81.
Office Action—First for Chinese application No. 200380103057.4, dated Nov. 10, 2006 (English translation).
Office Action—Second for Chinese application No. 200380103057. 4, dated Jun. 22, 2007 (English translation).
Office Action: Rejection Decision for Chinese application No. 200380103057.4, dated Mar. 28, 2008 (English translation).
Office Action: Notification of Reexamination for Chinese application No. 200380103057A, dated Apr. 8, 2009 (English translation).
Office Action—First for Chinese application No. 200810135762.7, dated Jun. 10, 2010 (English translation).
Office Action—Second for Chinese application No. 200810135762. 7, dated Oct. 25, 2011 (English translation).
Office Action: Rejection Decision for Chinese application No. 200810135762.7, dated Aug. 3, 2012 (English translation).
Office Action: Notification of Reexamination for Chinese application No. 200810135762.7, dated Aug. 1, 2013 (English translation).
Office Action—First for Chinese application No. 201280023319.5, dated Oct. 20, 2014 (English translation).
Office Action for Japanese application No. 2004-550983, dated Jan. 19, 2010 (English translation).
Office Action: Decision Refusal for Japanese application No. 2004-550983, dated Aug. 24, 2010 (English translation).
Office Action: PreTrial Re-Examination for Japanese application No. 2004-550983, dated Jan. 31, 2012 (English translation).
Office Action: Trial Decision for Japanese application No. 2004-550983, dated May 21, 2013 (English translation).
Office Action for Japanese application No. 2010-288189, dated Jan. 8, 2013 (English version).
Office Action: Notice of Allowance for U.S. Appl. No. 13/755,279, dated Jan. 30, 2015.
Office Action-First: for Japanese application No. 2014-503150, dated Feb. 24, 2015 (English translation).
Office Action for Chinese application No. 200810135762.7, dated Jun. 8, 2015 (English translation).
Office Action for Chinese application No. 201280023319.5, dated May 26, 2016 (English translation).
Office Action for Russian application No. 2013149419, dated Apr. 18, 2016 (English translation).
Sephadex LH-20 (product data accessed via hittp://www.gelifesciences.com/webapp/wcs/stores/servlet/ProductDisplay?categoryId=11520&catalogId=10101&productId=20936&storeId=11787&langId=-1 on Apr. 7, 2016).
Office Action for Chinese application No. 200810135762.7, dated Aug. 19, 2016 (English translation).

(56) References Cited

OTHER PUBLICATIONS

Office Action for Israel application No. 228757, dated Feb. 2, 2017 (English translation).
Office Action: Notification of Reexamination for Chinese application No. 201280023319.5 and Exhibits 1-3, dated Mar. 3, 2017 (English translation).
Office Action for Korean application No. 10-2017-7016140, dated Aug. 21, 2017 (English translation).
Office Action for Australian application No. 2016265998, dated Jul. 15, 2017.
Office Action for Japanese application No. 2015-209955, dated Oct. 4, 2016 (English translation).
Office Action—First for Mexican application No. MX/a/2013/011650, dated Jan. 11, 2017 (English translation).
Office Action for Chinese application No. 200810135762.7, dated Jan. 24, 2017 (English translation).
Office Action for Korean application No. 10-2013-7029263, dated Feb. 13, 2017 (English translation).
Office Action for Canadian application No. 2,831,697, dated Oct. 26, 2017.
Office Action for Russian application No. 2016137782, dated Sep. 9, 2017 (English translation).

* cited by examiner

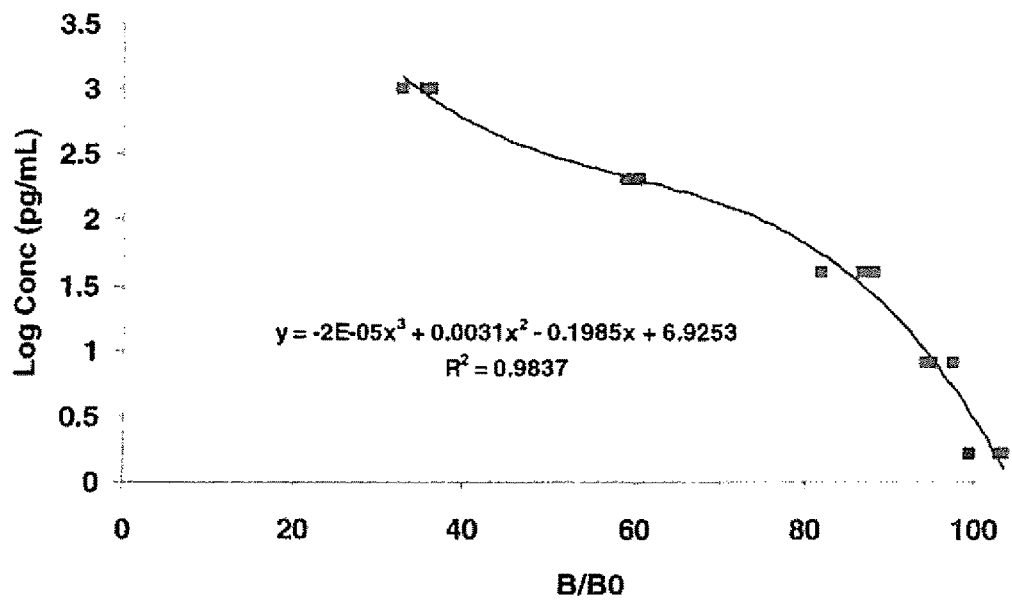
Figure 1 Panel a)
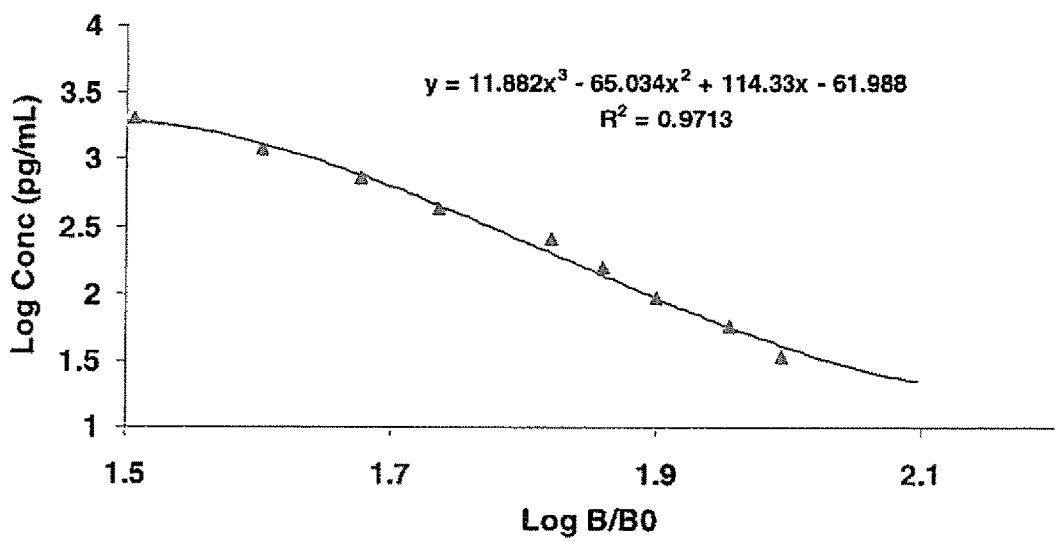
Figure 1 Panel b)

PROCESS FOR THE PREPARATION OF A SULFATED DERIVATIVE OF 3,5-DIIODO-O-[3-IODOPHENYL]-L-TYROSINE

CROSS-REFERENCE TO RELATED APPLICATIONS

This application is the national stage application of corresponding international application number PCT/EP2012/056274, filed Apr. 5, 2012, which is a continuation in part of U.S. Ser. No. 13/083,047, filed Apr. 8, 2011; this application claims priority to and the benefits of both the Italian application no. MI2011A000713, filed Apr. 29, 2011, and the U.S. Ser. No. 13/083,047, filed Apr. 8, 2011, all of which are hereby incorporated by reference in their entirety.

FIELD OF THE INVENTION

The field of the present invention relates to a process for the preparation of sulfated derivatives of thyroid hormones or salts thereof.

BACKGROUND OF THE INVENTION

Thyroid hormone tri-iodothyronine (3,5-diiodo-O-[3-iodophenyl]-L-tyrosine or T3) is the metabolically most active thyroid hormone. Like thyroxine (T4) it is physiologically produced by thyroid and stored together with it, under the form of a thyroglobulin, a glycoprotein precursor. On average, one thyroglobulin molecule contains three or four T4 residues and, at the most, one T3 residue. TSH production activates thyroglobulin proteolysis through the enzymes cathepsin D, B and L with the release of thyroid hormones T3 and T4. However, T3 generation is not limited to this mechanism: actually, in the peripheral tissues, thyroxine is transformed into tri-iodothyronine (80% of tri-iodothyronine is periferally produced by thyroxine and 20% is produced inside thyroid gland).

The importance of T3 is not only the one due to the fact of being the most active thyroid hormone. Actually, in this respect, various pathological conditions are known that are caused by its deficiency. In particular, e.g., in nervous tissue during embryonal development and childhood, T3 deficiency gives rise to a reduction in cerebral and cerebellar cortex growth, axons proliferation, cell migration, myelinization, dendrite branching and synapse genesis. As a result of T3 deficiency in the initial stages of life, a delay in the nervous system development is observed followed by a cognitive and motor deficit, that may cause a clinical picture referred to as cretinism. Also in adults it has been demonstrated by cerebral PET that, when the tri-iodothyronine levels are reduced, the blood flow inside the brain and glucose cerebral metabolism are lower. These data may explain the psycomotor deficit in the hypothyroid individuals.

In addition to the effects observed in the nervous tissue, also the ones in the bone tissue are known where the endochondral ossification is stimulated by tri-iodothyronine, thus rendering the bone linearly longer through maturation of the epiphysis bone centers. Even if not necessary after birth for the bone linear growth, tri-iodothyronine is essential for the proper fetus bones development.

Furthermore, T3 effects in the epidermis tissues have been substantiated, where tri-iodothyronine not only takes part in its maturation and of skin adnexa, but also in degradation thereof thus promoting cell regeneration. Therefore, both the excess and the deficiency of this hormone can cause dermatological problems.

Therefore, T3 thyroid hormone may definitely be considered as a pleiotropic hormone, with well documented effects, in addition to the ones above mentioned, in the blood tissue, where it increases erythropoietin production and, consequently, haemopoiesis; in fat tissues, where it promotes maturation of pre-adipocytes to adipocytes, increases the fatty acids lipolysis and finally also regulating cholesterol metabolism. Hypothyroidism, very frequently generated by autoimmune pathologies, is rather common: actually, prevalence in Italian people is about 1.5% among females and 1% among males. It is pharmacologically treated in a satisfactory way through substitutive therapies, mainly based on synthetic levo-thyroxine (T4), drug of choice because of the very short half-life of the more active form, i.e. T3, which, for this reason, cannot be routinely used. However, also the therapy with levo-thyroxine shows some disadvantages connected to the fact that while plasmatic euthyroidism is restored, the tissutal one not always does. The study of pharmacological alternatives, such as the ones proposable on the basis of the thyromimetic T3 activity described in EP 1560575 B, might represent a desirable alternative to the present treatments of choice.

However, as far as T3S is involved, the major obstacle seems to be represented by the difficulties met by a large scale synthesis. Actually, until now it has been possible to produce T3S only on a laboratory scale.

In this respect, the preparation of T3S from T3 by means of sulphating agents e.g. concentrated sulphuric acid ($H_2SO_4$) or chlorosulfonic acid (CSA) in large excess has been described, for example in U.S. Pat. No. 2,970,165 and *Biochim. Biophys. Acta*, 33, 461 (1959), that describe the preparation of T3S from T3 in solid form, by means of the direct addition of concentrated sulfuric acid, at low temperatures.

*Endocrinology*, Vol. 117, No. 1, 1-7 (1985) and *Endocrinology*, Vol. 117, No. 1, 8-12 (1985) envisage the synthesis of T3S from T3 by means of the addition under cooling of a chlorosulfonic acid (CSA) solution in dimethylformamide, followed by a purification step through Sephadex LH-20.

Up to now however, none of the prior art processes can be scaled up for grams production of the final product in a pure form, mainly because the reported purification procedures need extremely high volumes. Advantageously, is has now been found that the sulfation reaction starting from tri-iodothyronine with chlorosulfonic acid (CSA) as a sulfating agent, in the presence of DMAC, offers high conversion rates. Moreover the purification can be carried out with smaller volumes than the ones reported in the known prior-art processes. Eventually, the product T3S can be purified up to the required levels for its clinical use both for the necessary quality and quantity (hundreds of grams), also under conditions applicable on an industrial scale.

Furthermore, since only radioactive assays to detect T3S levels in serum, such as the RIA described in Chopra et al. (J. Clin. Endocrinol. Metab., 1992, 75: 189-194), have been described until now, the need exists for safer immunoassays based, for example, on non-radioactive reagents. The use of such a reagents would also allow clinical and/or research structures to carry out these measures. To this aim, non radioactive immuno-assays have been developed and are part of the present invention.
}

BRIEF DESCRIPTION OF THE DRAWINGS

FIG. 1. Panel a) T3S calibration curve by competitive ELISA; Panel b) DELFIA calibration curve. T3S was assayed at 33.6, 56, 93.3, 155.5, 259, 432, 720, 1200, 2000 pg/mL.

SUMMARY OF THE INVENTION

Figure 2:
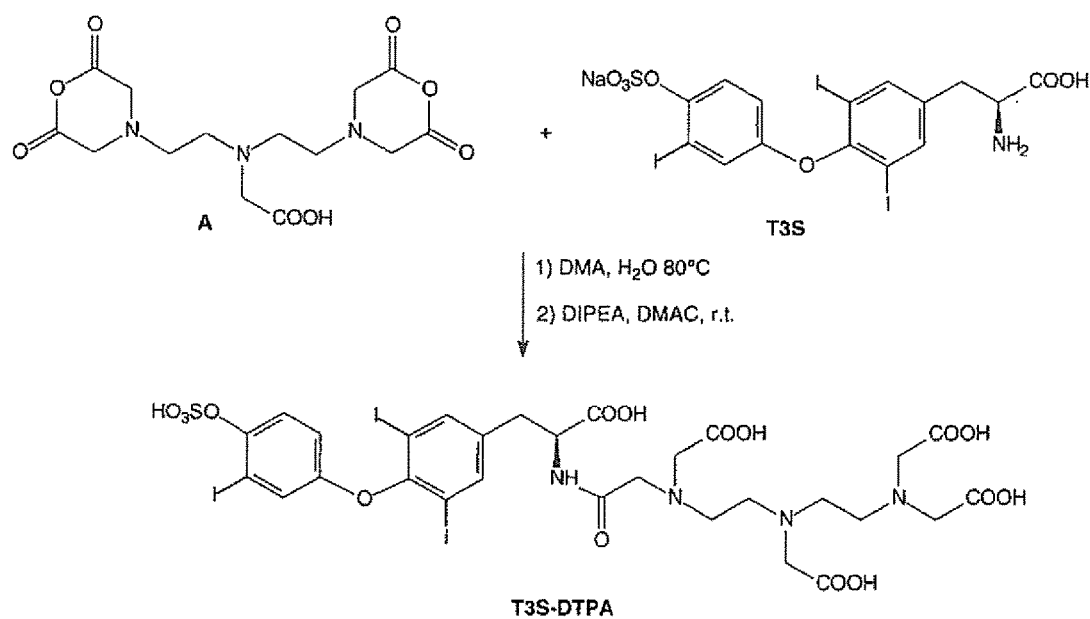
FIG. 2. Schematic of DTPA-T3S monoamide synthesis.

The present invention relates to a process for the preparation of a mono-cationic salt of 3,5-diiodo-O-[3-iodo-4-(sulfooxy)phenyl]-L-tyrosine of formula II (T3S), by starting from 3,5-diiodo-O-(4-hydroxy-3-iodophenyl)-L-tyrosine of formula I or a salt thereof, according to the scheme:

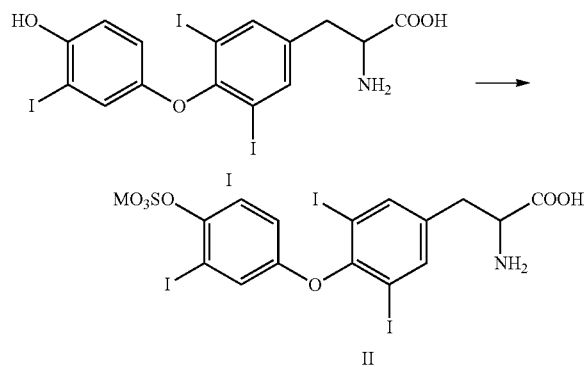

wherein M is an alkali metal, preferably Na, comprising the steps of:
a) sulfation of the compound of formula I or of the salts thereof with chlorosulfonic acid (CSA) in the presence of dimethylacetamide (DMAC) as a sovent;
b) salification of the sulfated derivative obtained in a) to give the compound of Formula II (T3S) by adding the reaction mixture obtained in a) to an aqueous solution of an alkali metal inorganic salt, preferably a mono-cationic sodium, even more preferably $NaHCO_3$.

According to a particularly preferred embodiment, the compound of formula I (T3) is obtained by means of the iodination of a compound of formula III (T2):

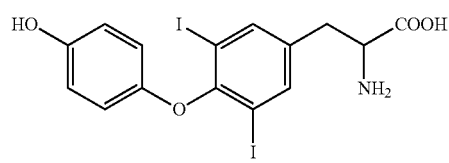

with an iodinating agent, preferably with NaI and $I_2$, in the presence of an aliphatic amine, preferably selected from linear mono alkyl ($C_1$-$C_4$) aliphatic amines, among which, ethylamine is preferred.

The addition of the iodinating agent is carried out in the presence of an aqueous solvent, preferably water, at a temperature preferably lower than 25° C. Preferably, the iodinating agent is present at a molar ratio comprised between 0.9 and 1.1 mol/mol of compound III (T2).

Thus the process for the preparation of T3S comprises the preparation of T3 by means of the iodination of T2 under the conditions above described and then its sulfation with chlorosulfonic acid in dimethylacetamide, as better described in the detailed description.

Moreover, according to a further aspect, the invention also comprises the formulation of the active principle, T3S, into pharmaceutical compositions, preferably solid, wherein T3S, preferably under a powder form, is mixed with a diluting agent and then a flowing agent, a lubricating agent, preferably glicerol dibeenate, and a disaggregating agent, preferably croscaramellose or the derivatives thereof, are added to the mixture their sieving and their further mixing with the diluting mixture comprising the active principle.

Thus according to this realization, the process comprises a step where the diluent, for example microcrystalline cellulose, is added in one or more fractions, their mixing, then the preparation of a mixture comprising a flowing agent, preferably glicerol dibeenate, a lubricating agent, preferably magnesium or zinc stearate, hydrated colloidal silica, colloidal silicon dioxide and preferably also a disintegrating agent, preferably croscaramellose or the derivatives thereof; then their sieving and their further mixing with the mixture comprising the active principle together with the diluent. Further excipients, stabilizers and diluents (such as for example calcium carbonate) may then be added and mixed for a variable time.

According to a particularly preferred aspect, the invention further discloses a tablet prepared by the process above described, comprising T3S as the active principle in a quantity comprised from 1 to 1000 µg and comprising the following diluents, excipients, glidants and lubricants: calcium carbonate, glycerol dibeenate, croscarmellose sodium salt, hydrate colloidal silica, magnesium stearate, microcrystalline cellulose. Preferred quantities for a single dosage are given in the table below:

|  | Amount per Tablet |
| --- | --- |
| Calcium carbonate | 20-40 mg |
| Glycerol dibeenate | 2-15 mg |
| Croscarmellose sodium salt | 1-10 mg |
| Hydrate colloidal silica | 0.1-5 mg |
| Magnesium stearate | 0.01-2 mg |
| Microcrystalline cellulose | At least 30 mg |

A further embodiment of the invention is represented by non radioactive immunoassays.

Preferably the immunoassay is an Enzyme Linked Immuno Assay (ELISA), more preferably a competitive ELISA, more preferably carried out in a multi-well plate, using as detectable moiety a fluorescent group or an enzyme (e.g., horseradish peroxidase, alkaline phosphatase, etc.) or an avidin-derivative detectable moiety (i.e. biotin).

As a further development of the T3S non-radioactive detection assays, reagents have been developed for the Lanthanide Fluorescence Immuno-Assay. This assay, the synthesized reagents, and kits for T3S quantitation based on the new reagents, represent a further object of the invention.

DETAILED DESCRIPTION OF THE INVENTION

Object of the present invention is a process for the preparation of a sulfated form of the thyroid hormone T3, 3,5-diiodo-O-[3-iodo-4-(sulfooxy)phenyl]-L-tyrosine (T3S) having formula II as a mono-cationic salt, by starting from 3,5-diiodo-O-[4-hydroxy-3-iodophenyl]-L-tyrosine of formula I or from a salified derivative thereof:

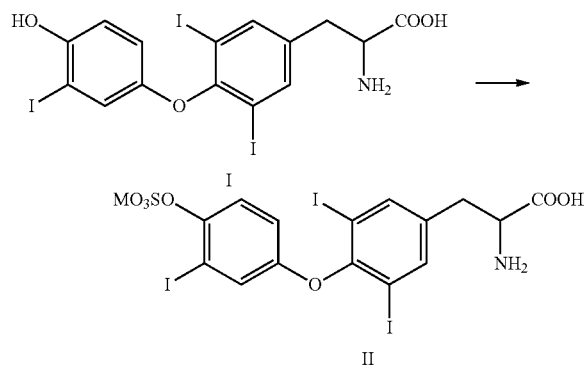

wherein M is an alkali metal, preferably Na, which comprises the steps of:
a) sulfation of the compound of formula I (T3) with chlorosulfonic acid (CSA) in the presence of dimethylacetamide (DMAC) as a sovent,
b) salification of the sulfated derivative obtained in a) to give the compound of formula II. Salification is generally obtained by means of the addition of the reaction mixture obtained in a) to an aqueous solution of an alkali metal inorganic salt, preferably a sodium salt, even more preferably $Na_2CO_3$ or $NaHCO_3$.

For the purpose of the present invention by T3S is meant the compound of Formula II comprising either the sulfated form of tri-iodothyronine or the mono-cationic salts thereof (Formula II compound).

Step a) is carried out by adding CSA to a suspension of T3 in DMAC under cooling, while keeping the solution under a vigorous stirring. Temperature is kept at values lower than about 10° C., more preferably comprised between −10° C. and 8° C., more preferably between −8° C. and 6° C., even more preferably between −5° C. and 5° C.

The addition of CSA to the suspension is made slowly, preferably in a period of time comprised from 30 to 60 min depending on the amount of the reagents employed and preferably under an inert atmosphere, for example under a nitrogen or argon atmosphere.

According to a preferred embodiment, the molar ratio between CSA and T3 is greater than 4, preferably comprised from 4.5 to 10, even more preferably comprised from 7 to 9. Even more preferably comprised from 7.5 to 8.5 mol of CSA/mol of T3. The concentration of T3 in DMAC, expressed as mol of T3/L of DMAC, is comprised from 0.06 to 0.15 mol/L, more preferably from 0.12 to 0.14 mol/L. It follows that, the ratio between CSA and solvent may be comprised from 0.35 to 1.28 mol of CSA/L of DMAC, preferably from about 0.8 to 1.15 mol/L, even more preferably from about 0.96 to 1.1 mol of CSA/L of DMAC.

After adding CSA, the mixture is allowed to react for a period of time not higher than 4-5 hours, generally without cooling, allowing the temperature to reach room temperature (20-25° C.).

Sulfation is generally completed, under the described conditions, when more than 85%, preferably more than 90%, even more preferably more than 95% T3 has been converted to T3S.

According to a particularly preferred embodiment, step a) of the process foresees the addition of CSA to a T3 solution in DMAC at a concentration of 0.12-0.14 mol of T3/L of DMAC, with a preferred ratio of about 8 moles of CSA per mole of T3, at a temperature comprised from about −5° C. to about 5° C., in a period of time of 30-40 min. At the end of the addition, cooling is generally stopped and the temperature is allowed to rise to room temperature (comprised from about 15 to 25° C.), for not more than 4-5 hours, preferably not more than 2-3 hours.

The sulfation mixture is then added according to salification step b), to an aqueous solution of an inorganic alkali salt, preferably mono-cationic, wherein Na is particularly preferred cation, in such an amount as to neutralize the present chlorosulfonic acid.

Salification is preferably carried out with an aqueous solution of sodium carbonate ($Na_2CO_3$) or sodium hydrogen carbonate ($NaHCO_3$), in amounts function of the amount of chlorosulfonic acid used in the former step, and at least sufficient to neutralize the pH of the resulting solution. In general, when $Na_2CO_3$ is used, an amount of about 1.5 moles per mole of CSA is sufficient. According to this embodiment, the $Na_2CO_3$ solution concentration is about 0.7 mol/L of solution. Under such conditions a solution pH after quenching comprised between 6.5 and 7.5 is obtained.

According to this embodiment, the corresponding mono-cationic salt of the T3S compound obtained, has formula II, wherein M is preferably Na.

The addition of the reaction mixture according to step b) is carried out in a period of time which is variable, typically comprised from 1 h and 3h, while keeping a temperature lower than 30° C.

The T3S compound of formula II, obtained in solution as a mono-cationic salt according to the step b) above described, is purified by chromatography, in accordance to a further step c). Chromatography is previously and optionally preceded by precipitation and/or filtration, for example gravimetrical or under vacuum, of the reaction mixture obtained in b), with the aim of reducing part of the inorganic salts that are formed as by-products.

Chromatography (c) is carried out on an adsorbent resin, of the polymer type. Preferably, such a resin is constituted by a macro reticular aromatic polymeric matrix. Examples of preferred resins are XAD™ Amberlites™, even more preferably Amberlite™ XAD™ 1600.

As well known, before its use, the resin is activated by means of procedures known in the art, such as, for example, washings with water, acetone or the like (for a general reference, see Rohm and Haas in "*Laboratory Column Procedures and Testing of Amberlite and Duolite Polymeric Adsorbents*", section "*Preparation of Resins*"). In accordance with the process of the invention the resin is preferably activated with the solvent selected for the next elution (i.e. acetone or a water/acetone mixture).

T3S is preferably eluted from the resin by an elution mixture of solvents with a decreasing gradient of polarity, starting from the mixture having higher polarity. According to a preferred embodiment, said elution mixture is at first water, followed by successive dilutions with a suitable polar organic solvent, in suitable reciprocal ratios.

Preferred elution mixtures are represented by water/acetonitrile and water/acetone in ratios comprised from 1:0 to 0.7:0.3. Preferably the elution mixture is represented by a mixture of water and acetone in a ratio comprised from 1:0 to 0.85:0.15 and the elution rate through the column is generally comprised from 0.9 to 1.1 volumes of column/h.

The fractions eluted from the column and containing the final product with a purity level higher than 95%, more preferably higher than 96%, 98%, 99% (measured by analytical methods well known in the art, such as for example UV detection and analysed by HPLC analysis) are collected together and the active principle can be isolated by evaporating the solvent, i.e. under vacuum by freeze-drying or by other known methods.

However, according to a preferred embodiment, the eluted fractions are concentrated for example by partial evaporation under vacuum up to a concentration of about 10 g/kg of solution.

At this concentration, the pH of the solution is adjusted to values lower than 6.5, preferably comprised from 5.5 to 6.5, by adding a diluted strong inorganic acid solution, preferably one acid selected between sulfuric acid and hydrochloric acid, being hydrochloric acid particularly preferred, and utilized in diluted form at a concentration comprised from 0.9 to 1.1 N.

The solution is further concentrated about 10-15 times and T3S can be isolated as a solid for example by freeze-drying, spray-drying, or, preferably treated with an organic solvent, preferably of a polar type to be isolated in solid form and then optionally further micronized.

Thus, according to this preferred embodiment, the Formula II compound is isolated in a solid form by treatment with a solvent selected from the group consisting of: acetone, acetonitrile and $C_1$-$C_4$ alchools. However other solvents may be employed, which are selected among: aromatic alkanes, ethers, chlorinated solvents, esters, dimethylformamide, nitrometane, dimethylsulfoxide, 2-methoxyethanol, or mixtures thereof, that allow to obtain a salt in solid form, and isolable.

Thus, in detail, after chromatography and concentration of the T3S containing fractions up to a concentration of about 10 g/kg of solution, pH adjustment to values lower then 6.5, preferably comprised from 5.5 to 6.5, and further evaporation up to a concentration of the Formula II compound comprised from 170 to 500 g/kg of suspension or gel, the concentrated solution is treated with an organic solvent. Preferably, said solvent is a polar organic solvent selected among: acetone, lower alchools, such as for example, ethanol, propanol, isopropanol, and the like, and acetonitrile, being acetone particularly preferred.

The addition of acetone to the concentrated T3S solution occurs at a temperature comprised from 20 to 25° C., preferably leaving the mixture under stirring for 1-3 h at a temperature comprised from 0 to 25° C., in order to let the solid form of the mono-cationic T3S salt precipitate completely. The addition of the solvent to the suspension occurs according to known proportions: when acetone is used, it's added in an amount comprised between 1-11 g acetone/g T3S, at a temperature comprised from 20-25° C.

The mono-cationic derivative of formula II, or more preferably the sodium salt thereof, is thus obtained in solid form after separation of the liquid phase from the solid one, for example by filtration, with a HPLC purity higher than 95%, more preferably, higher than 96%, 98% or even >99%. Thus, taken as a whole, the process according to the invention allows to obtain isolation of the final product (T3S) in high yields (overall yield: ≥60%) and with a high purity level (HPLC >99%).

Actually, advantageously with prior art processes, already in the sulfation mixture a) in the presence of DMAC, the amount of by-products is lower than 10%, generally lower than 7%.

The high conversion percentage in the sulfation reaction and the following salification allow then to obtain a product in pure form by an industrially applicable chromatographic step and with limited volumes.

T3S is efficiently separated from the other by-products and has high purity (>99%) even when it is prepared in hundreds of grams thus rendering the use of this tri-iodothyronine derivative in clinical practice possible.

In order to prepare formulations for clinical use, T3S, in solid form and with a purity up to 99%, is preferably further micronized, for example under nitrogen pressure, to reduce the particle size.

Particularly preferred is a particle size smaller than 25 μm (at least 90%, more preferably at least 95% of the particles with dimensions lower than 25 μm) resulting stable for at least one month when submitted to accelerated stability trials in a climatic chamber.

Therefore, according to a preferred aspect of the invention, the process comprises micronization of the solid T3S in a pure form, to give particles of the above defined size and the use thereof to prepare solid formulations, for oral administration.

According to this aspect, after micronization, T3S is formulated together with suitable additional components in powder mixtures, optionally also under granular or microgranular form, preferably formulated as tablets or pills obtained through direct compression of the powder mixture.

The T3S formulation in solid form or more preferably into tablets, provides to add, to the micronized active principle (or principles when preferably in combination with levo-thyroxine), firstly a part of the amount of the necessary final diluent, preferably 30, 40, or preferably at least 50% of the diluent, and mixing them to give mixture a).

Preferred diluent is cellulose or the derivatives thereof for example microcrystalline cellulose. Other suitable diluting agents are caolin, starch or alkali inorganic salts such as magnesium or calcium carbonate. Particularly preferred is calcium carbonate, more preferably in association with microcrystalline cellulose.

Mixture a) is then mixed with a mixture b) comprising further components, in general: a glidant agent, a lubricating agent and a disaggregating agent, their sieving and their successive mixing with mixture a) comprising the active principle.

Among the disintegrating agents, particularly preferred is croscaramellose or its derivatives. Other usable agents to this aim are crospovidone, polymethacrylates, maltodestrines, starch sodium glicolate, pre-gelatinized starch, sodium alginate.

Among glidant agents, particularly preferred is glicerol dibehenate. Other usable glidants are: tribasic calcium phosphate, talc, starch or derivatives thereof.

Among the lubricating agents particularly preferred are magnesium or zinc stearate, colloidal hydrated silica, colloidal silicon dioxide. Further excipients, stabilizers and diluents (such as for example calcium carbonate) may be successively added and mixed for a variable time. The final mixture is then measured out and the tablets are preferably prepared by direct compression.

T3S is present in the solid dosage units in amounts comprised from 1 and 1000 μg, more preferably from 2.5 to 500 μg, even more preferably from 5 to 250 μg, as the only active principle, or in combination with other active principles, preferably T4 (levo-thyroxine). According to this embodiment T4 is present in amounts comprised from 1 to 800 μg, or from 5-400 μg, more preferably from 10-200 μg. Accordingly then, in the preparation process of tablets comprising both T3 and T4 as active principles, these are mixed with the preferred diluent(s) in mixture a) and further mixed with the other components, in their turn pre-mixed, as above described.

Therefore according to a preferred aspect the invention discloses a tablet prepared by the process above described, comprising T3S as the active principle, in a quantity comprised from 1 to 1000 μg together with the following additional components:

the diluent, selected from cellulose or derivatives thereof, preferably together with a second diluent, preferably calcium carbonate, up to 35% of the total diluent (w/w);

the glidant, selected from glycerol dibehnate (most preferred), talc, silica derivatives among which magnesium trisilicate, amides, tribasic calcium phosphate, are usually present in the composition in a quantity range from 1 to 10%, most preferably 4 to 6% (w/w);

the disintegrant selected from starch, croscarmellose sodium and crospovidone. Preferred is croscarmellose sodium salt in a quantity ranging from 0.5 to 10% even more preferably comprised from 1-5%, most preferably comprised from 2- to 4% (w/w);

the lubricant selected from magnesium stearate, hydrate colloidal silica and talc, more preferably magnesium stearate and colloidal silica, in a total quantity range comprised from 0.1 to 7% even more preferably the first one comprised from 0.1 to 2% and the second comprised from 0.5 to 5% (w/w).

Particularly preferred as excipients are the following ingredients: calcium carbonate, glycerol dibehenate, croscarmellose sodium salt, hydrate colloidal silica, magnesium stearate, microcrystalline cellulose, according to the following preferred quantities:

|  | Amount per Tablet |
| --- | --- |
| Calcium carbonate | 20-40 mg, preferably 25-35 mg, more preferably 30 mg |
| Glycerol dibehenate | 2-15 mg, preferably 4-8 mg, more preferably 5 mg |
| Croscarmellose sodium salt | 1-10 mg, preferably 2-6 mg, more preferably 3.5 mg |
| Hydrate colloidal silica | 0.1-5 mg, preferably 0.5-4, more preferably 2 mg |
| Magnesium stearate | 0.01-2 mg, preferably 0.1-1 mg, more preferably 0.5 mg |
| Microcrystalline cellulose | At least 30 mg |

In a more preferred embodiment, the composition comprises 2.5 to 500 μg $T_3S$ or more preferably 5-250 μg $T_3S$.

For combination compositions where also T4 is present, T3S is preferably present in a quantity of from 2.5-500 μg and $T_4$ of from 1 to 800 μg, or, even more preferably: $T_3S$: 5-250 μg and $T_4$: 5-400 μg, or $T_3S$: 10-100 μg and $T_4$ 10-200 μg.

It is intended that the above quantities refer to single dosage units, preferably tablets of about 110 mg, preferably for daily single dosage administration, even though the skilled artisan may envisage adjustments due to alternative composition forms, tablet weight and/or therapeutic treatment protocols.

The tablets according to the preferred embodiment show optimal dissolution rates (see table below) and an optimal stability of the active principle(s) (at least 24 months).

The following properties measured in conditions according to ICH Guidelines:

| Dissolution test | ≥75% after 45' |
| --- | --- |
| Moisture content | ≤10% |
| Resistance to crushing | ≥20 N |
| HPLC Title T3S | 90-110% |
| HPLC Title T4 (when present) | 90-110% |

In the process according to the invention all the reagents including T3 (compound of formula I), are commercially available.

However, according to a particularly preferred embodiment, T3 is prepared by iodination of a compound of formula III (3,5-diiodo-thyronine, Levoditi, or T2):

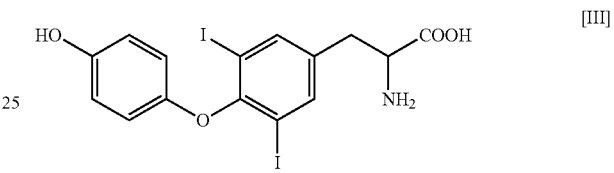

with an iodinating agent, preferably NaI and $I_2$, in the presence of an aliphatic amine, preferably selected among the mono-alkyl ($C_1$-$C_4$) linear aliphatic amines, among which the preferred is ethylamine. T2 is preferably prepared as described.

The addition of the iodinating agent is carried out in the presence of an aqueous solvent, preferably water, at a temperature preferably lower than 25° C.

Preferably the iodinating agent is present at a molar ratio comprised from 0.9 to 1.1 mol/mol of compound III (T2).

After iodination, T3 is isolated, preferably by filtration, as sodium salt, then converted in acid form by re-suspension in water and acidification with an acid, preferably acetic acid or sulfuric acid.

The acid form is isolated, preferably by filtration, again re-suspended in water to remove salts and filtered.

T3, as a wet solid, is suspended in N,N-dimethylacetamide, the suspension is anhydrified and submitted to sulfation reaction.

According to a preferred realization, the molar ratio between CSA and T3 is greater than 4, preferably comprised from 4.5 to 10, even more preferably comprised from 7 to 9. Even more preferably comprised from 7.5 to 8.5 mol of CSA/mol of T3. The concentration of T3 in DMAC, expressed as mol of T3/L of DMAC, is comprised from 0.10 to 0.15 mol/L, more preferably from 0.12 to 0.14 mol/L. It follows that, the ratio between CSA and solvent may be comprised from 0.58 to 1.28 mol of CSA/L of DMAC, preferably from 0.89 to 1.15 mol/L, even more preferably from 0.96 to 1.09 mol of CSA/L of DMAC.

After adding CSA, the mixture is allowed to react for a period of time not higher than 4-5 hours, generally without cooling, allowing the temperature to rise to room temperature.

Sulfation is generally completed, under the described conditions, when more than 85%, preferably more than 90%, even more preferably more than 95% T3 has been converted to T3S.

According to a particularly preferred embodiment, step a) of the process foresees the addition of CSA to a T3 solution in DMAC at a concentration of 0.12-0.14 mol of T3/L of DMAC, with a preferred ratio of about 8 moles of CSA per mole of T3, at a temperature comprised from about −5° C. to about 10° C., in a period of time of 30-40 min. At the end of the addition, the cooling is generally stopped and the temperature is allowed to rise to room temperature (comprised from about 15 to 25° C.), for not more than 4-5 hours, preferably not more than 2-3 hours.

The sulfation mixture is then added according to salification step b), to an aqueous solution of an inorganic alkali salt, preferably di-cationic, wherein Na is a particularly preferred cation, in such an amount as to neutralize the present chlorosulfonic acid.

Salification is preferably carried out with an aqueous solution of $Na_2CO_3$ or $NaHCO_3$, in amounts function of the amount of chlorosulfonic acid used, at least sufficient to neutralize the pH of the resulting solution. In general, when $Na_2CO_3$ is used, an amount of salt of at least 1.5 moles per mole of CSA is sufficient. When, according to a particularly preferred aspect, the inorganic alkali metal salt is $Na_2CO_3$, its final concentration is at least 0.7 mol/L solution. Under such conditions, after quenching, a pH of the solution comprised from 6.5 to 7.5 is obtained.

According to this embodiment, the corresponding monocationic salt of the T3S compound obtained, has formula II, wherein M is preferably Na.

The addition of the reaction mixture according to step b) is carried out in a period of time which is variable, typically comprised from 1 h and 3 h, while keeping a temperature lower than 30° C.

The T3S compound of formula II, obtained in solution as a mono-cationic salt according to steps b) and c) as above described.

The process according to the invention describes for the first time, according to the Applicant's best knowledge, the preparation of $T_3S$. from either T3 or T2, at a purity of at least 95%, more preferably, of at least 96%, 98% or >99%, for clinical use.

According to a further embodiment, the invention also relates to a non-radioactive $T_3S$ immunoassay, either based on colorimetric, fluorescent or chemiluminescent detection.

Preferably the immunoassay is an Enzyme Linked Immuno Assay (ELISA), more preferably is a competitive ELISA where increasing amounts of $T_3S$. compete for the binding to a solid phase bound anti-$T_3S$ antibody, (e.g. the polyclonal disclosed in Chopra et al., J. Clin. Endocrinol. Metab., 1992, 75: 189-194) with a fixed amount of $T_3S$ conjugated with a detectable moiety, such as a fluorescent group or an enzyme (e.g. horseradish peroxidase, alkaline phosphatase, etc.) or an avidin binding-derivative (i.e. biotin) optionally linked to a detectable moiety.

The $T_3S$ derivatives useful for the non radioactive assays are generally comprised in the general Formula A:

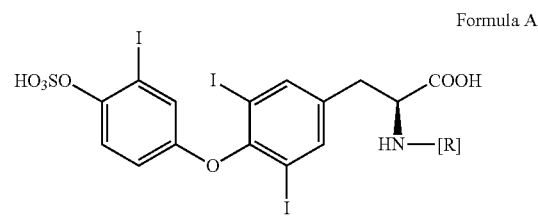

Formula A wherein R is selected from the group consisting of:
a) a detectable moiety, selected from the group consisting of: a fluorescent group or an enzyme selected from the group consisting of: horseradish peroxidase, alkaline phosphatase,
c) an avidin-binding derivative optionally linked to a detectable moiety,
d) a lanthanide chelating agent.

When R is a lanthanide chelating agent the $T_3S$ derivative is preferably the compound of Formula IV.

The assay is preferably carried out in a multi-well plate. Preferably, the detectable moiety is a fluorescent group or an enzyme (e.g., horseradish peroxidase, alkaline phosphatase, etc.) or an avidin-binding-derivative (i.e. biotin). According to the latter embodiment, detection is preferably carried out with an avidin-derivative, preferably streptavidin comprising an enzyme such as Alkaline Phosphatase or Horseradish Peroxidase, preferably HRP, which converts specific substrates into coloured, fluorescent or chemiluminescent products. The use of biotin-avidin interaction, combined with the various detection luminescence as techniques for signal development, allows signal amplification and increased sensitivity comparable to a RIA test (see i.e. Chopra et al., J. Clin. Endocrinol. Metab., 1992, 75: 189-194) but without the need for radioactivity, a clear advantage over the prior art.

The ELISA assay, the $T_3S$-derivatives, such as the biotin derivative their synthesis and kits for T3S quantitation comprising such reagents, represent a further objects of the present invention.

As an alternative embodiment the non-radioactive $T_3S$ immunoassay is developed for a fluorescence technique, called Lanthanide Fluorescence Immuno-Assay, described in Hemmilä I et al. Anal Biochem. 1984 March; 137(2): 335-43, by which a sensitivity from 1-1000 pg/ml $T_3S$ is obtained. This assay developed for T3S detection, the synthesized reagents, and kits for T3S quantitation comprising said reagents, represent a further object of the invention.

Thus, accordingly, a DTPA-$T_3S$ monoamide(3,5-Diiodo-N-[[(carboxymethyl)[2-[(carboxymethyl)[2-[bis(carboxymethyl) amino]ethyl]amino]ethyl]amino]acetyl]-O-[3-iodo-4-(sulfooxy)phenyl]-L -tyrosine) of Formula IV, represents a chelating compound according to a preferred embodiment:

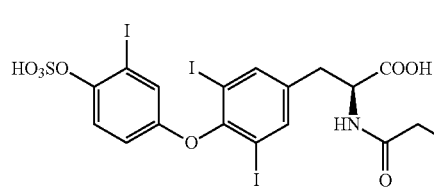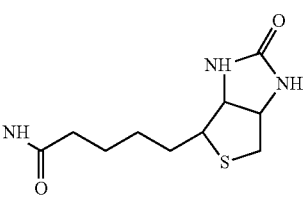

Formula A'

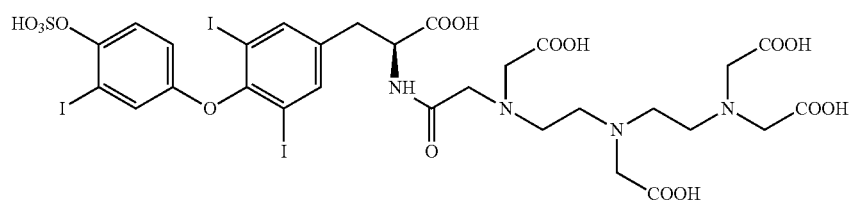

Formula IV

Other molecules can be designed and synthesized by an expert in the field, through conjugation of T₃S with a variety of chelating moieties, among those suitable for complexation of lanthanide ions, e.g., nitrilotriacetic acid (NTA), ethylenediaminetetraacetic acid (EDTA), ethylenediamine-N,N'-bis(2-hydroxyphenylacetic acid) (EDDHA), ethylenediaminedisuccinic acid (EDDS), propanediaminetetraacetic acid (PDTA), diethylenetriaminetetraacetic acid (DTTA), diethylenetriaminepentaacetic acid (DTPA), and similar molecules. Conjugation between the chelating agent and T₃S can be obtained by a variety of methods known to the expert in the field, including a direct amide bond formation, as exemplified in Experimental Part, or the use of bifunctional chelating agents, that may even be commercial products, such as (S)-1-p-isothiocyanatobenzyldiethylenetriaminepentaacetic acid (DTPA isothiocyanate—Invitrogen cat. I24221), or similar products.

Suitable lanthanide metals to be used as chelate labels are selected in the group consisting of: samarium, terbium, dysprosium and europium. Particularly preferred is the Europium chelate 3,5-Diiodo-N-[[(carboxymethyl)[2-[(carboxymethyl)[2-[bis(carboxymethyl)amino]ethyl]amino]ethyl]amino]acetyl]-O-[3-iodo-4-(sulfooxy)phenyl]-L-tyrosine (Formula V).

chelated product can be desalted by adsorption on a resin column (e.g. Amberlite XAD1600) and elution with water/solvent mixtures.

Also in this case, a sensitivity comparable to the known RIA test (see Chopra et al., ibidem) is obtained while avoiding the use of radioactive isotopes which represents a clear advantage over the prior art assay.

From the above teachings the skilled man may envisage alternative formats of the ELISA which are nevertheless comprised in the present invention. For instance, the target hormone T₃S can be covalently bound to the plate and the antibody, optionally linked to a tracer enzyme or used in combination with an antibody linked to a tracer enzyme, used to competitively measure T3S level in an unknown sample. According to a further embodiment, the tracer is the antigen itself (T₃S) directly bound to a detectable enzyme (e.g., Alkaline Phosphatase or Horseradish Peroxidase) according to procedures known to the skilled man, also available in ready-to-use conjugation kit.

According to a further embodiment, the invention comprises a kit for T₃S administration and dosage in serum, wherein said kit comprises a dosage kit for T₃S immunodetection by the above disclosed non-radioactive assays and an administration/therapeutic kit with a number of T₃S or

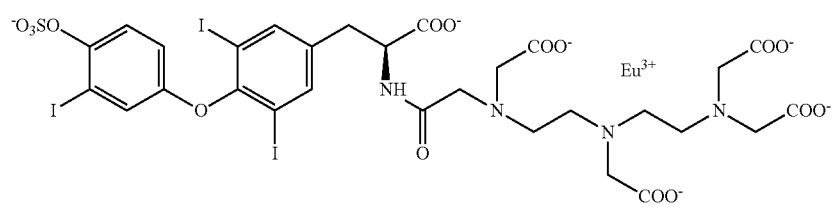

Formula V

A schematic of its synthesis is shown in FIG. 2. The process can be summarized as follows: DTPA di-anhydride is partially hydrolysed by adding an approximately equimolar amount of water dissolved in a suitable organic solvent, then the product, mainly composed of DTPA mono-anhydride is reacted with T₃S, in the presence of a suitable organic or inorganic base. After solvent evaporation, the oily residue is diluted with water. The resulting precipitate is collected, washed with water and dissolved in a water/acetone mixture. This crude reaction product is purified on a column of Amberlite XAD1600, or similar resin, developed with mixtures or gradients of water/acetone. The product containing fractions are collected and evaporated to dryness, yielding the desired DTPA-T₃S monoamide. Lanthanide complexation is obtained according to known procedures by adding an equimolar amount of a lanthanide salt to the monoamide water solution and adjusting the pH at 7 with a suitable base (e.g. NaOH). Optionally, the lanthanide T₃S and T4 composition daily doses (i.e. the weekly, biweekly, monthly or bi-monthly need), preferably in the form of tablets as described above.

The dosage kit for T₃S non radioactive immunodetection may comprise according to a first preferred embodiment, polyclonal antibodies, the avidin-binding T₃S derivative, wherein preferably the conjugate is T₃S-biotin and the avidin-derivative detectable moiety is i.e. streptavidin. More preferably, the avidin-derivative is streptavidin and the detectable moiety comprises an enzyme chemiluminescent moiety (such as Alkaline Phosphatase or Horseradish Peroxidase), preferably HRP.

According to the lanthanide fluorescence immunoassay derived embodiment, the kit may comprise, together with antibodies, reagents specifically developed for such a detection, such as a lanthanide metals chelated complex T₃S derivatives, wherein the metal is selected in the group consisting of: samarium, terbium, dysprosium and europium. Particularly preferred is the Europium chelate 3,5-

Diiodo-N-[[(carboxymethyl)[2-[(carboxymethyl)[2-[bis(carboxymethyl)amino]ethyl]amino]ethyl]amino]acetyl]-O-[3-iodo-4-(sulfooxy)phenyl]-L-tyrosine (Formula V compound).

The kit may also comprise $T_3S$ standards for the preparation of a calibration curve. The standard may be pre-diluted and ready for use as a solution at the correct concentration or for solubilisation in a suitable solvent. The kit may also comprise other reagents selected from the group consisting of: a diluent, a dye-molecule, a buffer, a preservative, an anti-$T_3S$ antibody, an instruction leaflet.

The invention is now described by the following examples which are only explanatory and must not be construed as limitative of the scope of the invention.

EXPERIMENTAL SECTION

Example 1

Preparation of $T_3S$ in DMAC

All the amounts of the raw materials are expressed with reference to 100 g of T3.

3,5-diiodo-O-(4-hydroxy-3-iodophenyl)-L-tyrosine (100 g; 0.154 mol) was suspended in DMAC (2.0 L) under nitrogen atmosphere and vigorously stirred in order to avoid solid precipitation. After cooling to −5° C., CSA (142.2 g; 1.229 mol) was added dropwise in 40 min while keeping the temperature between −5÷5° C. At the end of the addition, cooling was stopped and the reaction mixture was left under stirring for about 4 h. The reaction mixture was added dropwise in 1.5 h, into a stirred aqueous solution of sodium bicarbonate (335.5 g; 3.994 mol in water, 4.5 L). At the end of the addition, from the so obtained solution with time it was observed the precipitation of a crystalline solid as a mixture of inorganic salts. Such a solid was filtered off, then the obtained solution was purified on Amberlite™ XAD™ 1600 by means of elution with water/acetone mixtures having decreasing polarity collecting the eluate into fractions. The fractions containing the product having an appropriate purity level were evaporated under vacuum up to a concentration of 10 g/kg. The pH of such suspension was adjusted to 6.2 with HCl 1N. The suspension was further concentrated up to a ratio of about 1:3 solid and residual water. Such a residue was treated with acetone under cooling for 2 h, then filtered off and washed with acetone. The product was dried at 40° C. under vacuum. 74 g of $T_3S$ were obtained as a white solid. Yield on the anhydrous base: 62%.

Example 2

Preparation of $T_3S$ from T2 (Levoditi)

The reaction schematic is presented below:

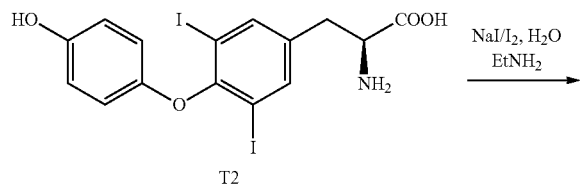

T2

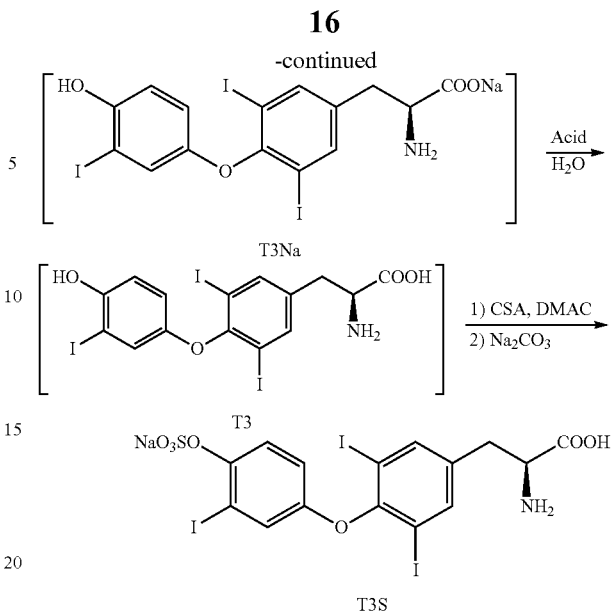

All quantities of raw materials are expressed for 1 kg of Levoditi.

Iodine (approx. 0.48 kg, source: SQM), NaI (approx. 0.65 kg, source: Ajay—SQM) and water were charged in a reactor 18-22° C. and stirred until complete dissolution. The resulting iodinating mixture was maintained under stirring at room temperature until use.

Levoditi obtained from L-thyrosine according to the process described in: Chalmers, J. R. et al. A. J. Chem. Soc. 1949, 3424-3433), NaI (approx. 0.32 kg) and water were charged in another reactor and 70% monoethylamine was added.

The iodinating mixture was added to the reaction mixture.

The suspension obtained was stirred for at least 6 h at 18-22° C., then was cooled to 0° C. in 1 h, stirred for 3-4 h and filtered. The cake was washed with water.

The wet solid was suspended in water and acetic acid was added to the mixture and stirred. The suspension was filtered and the cake washed with water.

The wet solid was re-suspended in water stirred, filtered and washed with water.

The cake was then suspended in DMAC (approx. 12.15 kg) and the suspension was anhydrified distilling under vacuum.

The suspension was cooled to 5-10° C. and, in nitrogen atmosphere, CSA (approx. 1.54 kg) was slowly added and the temperature maintained below 15° C.

The solution was heated to 18-22° C. in 1 h and maintained for another hour, then was added in a reactor containing a solution of $Na_2CO_3$ (approx. 2.27 kg) in water (approx. 29.02 kg), previously prepared, maintaining the temperature under 30° C.

The solution was purified onto a column of Amberlite XAD 1600 (12.5 L) by elution of water (87.5 L) and water/acetone mixtures (125 L) with decreasing polarity starting from 95:5 to 70:30. The fractions with high HPLC purity were collected and distilled under vacuum until the desired composition was achieved (approx. 0.04 kg $T_3S$/L suspension).

The suspension was cooled to 40° C. and Ethanol (approx. 5.22 kg) was added, obtaining a solution.

The mixture was cooled to 0° C. in 2 h, causing precipitation, stirred for another hour and then filtered. The cake was washed with Ethanol/water mixture at room temperature.

Wet solid was dried at approximately 40° C. under vacuum.

0.98 kg of pure T3-Sulfate sodium salt (HPLC Area %>99%) were obtained as a white solid.

Overall yield from T2 (on the anhydrous base): 68.5%.

Example 3

Preparation of $T_3S$ Tablets

The active principle, also in combination with different amounts of levo-thyroxine, was pre-mixed for fifteen minutes with 50% of the content of the microcrystalline cellulose.

To this pre-mixture the following ingredients were added in this order: glicerol dibehenate, colloidal hydrated silica, sodium croscaramellose, magnesium stearate and calcium carbonate (previously sieved through a 0.6 mm clean light/mesh sieve), together with the remaining 50% of the microcrystalline cellulose, mixing for further 20 minutes.

The uniformity of distribution of active principle in the mixture was checked by sampling from six points of the mixer; the text showed that the active principle (or the active principles) uniformly distribute within the mixture, also in the case of formulation with levo-thyroxine.

The powders mixture was then compressed by means of a rotary tablet press equipped with a round flat punch and the tablets were submitted to tests for friability, disaggregation times and the active principle or principles distribution.

The results of the texts performed on the mixing and pressing process confirmed reproducibility of both of them, for $T_3S$ dosages comprised from 25 to 200 μg. Moreover they showed that the tablets so obtained had parameters corresponding to the requirements provided for by the official European Pharmacopoeia (VI Ed.).

Tablet Composition

| | |
|---|---|
| $T_3S$ Na salt | 20.6 μg (corresp. to 20 μg $T_3S$) |
| Calcium carbonate | 30 mg |
| Glycerol dibehenate | 5 mg |
| Croscarmellose sodium salt | 3.5 mg |
| Hydrate colloidal silica | 2 mg |
| Magnesium stearate | 0.5 mg |
| Microcrystalline cellulose | Up to 110 mg |

The tablets prepared as above described were used in clinical trials Phase I on thyroidectomised individuals, showing that they can be used as a thyroid hormone replacement therapy (see US 2011/0245342).

In fact, $T_3S$ was shown to be absorbed (crossing the Gastrointestinal Barrier), was found in serum after oral administration and was converted to the clinically active T3 in a dose-related fashion. T3 levels in serum were still detectable 48 hrs after single dose administration.

Example 4

Quantitation of $T_3S$ by Immunoassay with Chemiluminescence Detection

Synthesis of T35 biotin derivative

Briefly, T3S biotin derivative was synthesized as follows: N-hydroxysuccinimidyl d-biotin-15-amido-4,7,10,13-tetraoxapentadecylate A (50 mg; 0.0849 mmol) was solubilized in DMAC (2 mL), to which DIPEA (14.5 uL; 0.0866 mmol) was added, while maintaining the reaction mixture under continuous stirring at 0° C. T3S (68.4 mg; 0.0908 mmol, prepared as described in Mol & Visser, Endocrinology 1985, 117:1-7) was then added and after a few minutes the suspension was left to heat up to room temperature to give a clear solution. It was allowed to stir for 2 h, then kept overnight at the same temperature. DMAC was evaporated under reduced pressure (10 mbar; 40° C.) to give a colourless oil. The crude so obtained was dissolved in H2O and purified by Semi-preparative HPLC. The fractions containing the product were collected, concentrated and finally lyophilized to give T3S-biotin as a white solid (59.6 mg; 0.0495 mmol). Yield 58%.

A polyclonal anti-T3S antiserum was obtained in rabbits as described in Chopra et al., J. Clin. Endocrinol. Metab., 1992, 75: 189-194.

The assay was based on a competitive ELISA in which increasing amounts of T3S competed for antibody binding with a fixed amount of $T_3S$ conjugated with biotin, in a white 96 well plate. The employment of the biotin-avidin interaction, which allows signal amplification, combined with luminescence as technique for signal development allowed for a sensibility comparable to the RIA test (described in Chopra et al., J. Clin. Endocrinol. Metab., 1992, 75: 189-194).

Standard solutions of T3S were prepared at the following concentrations: 1000, 200, 40, 8, 1.6 pg/mL in Diluent Buffer: PBS, 0.05% Tween, 0.3% BSA The tracer solution (T3S-Biotin, 180.6 μM) was prepared in the above diluent buffer. Antibody solution: T3S rabbit antiserum was diluted 1:50000 in Diluent Buffer plus 8 mM ANS (1-anilino-8-naphthalene sulfonate), 1.2 mg/mL Sodium Salicylate.

A 96 well white plate was coated over night at 4° C. with 100 μL/well of 2 μg/mL anti Rabbit IgG diluted in phosphate buffer pH 7.8. At the same time, Standard solutions of biotin labelled T3S were combined with the diluted antiserum and the T3S-biotin solution as reported in Table Table A. The mixed samples were incubated at room temperature in the dark, over-night. The day after, the plate was washed four times with Washing Buffer (0.05% Tween 20 in PBS), then incubated in Blocking Buffer (2% BSA in Washing Buffer) for 1 h at room temperature.

Afterwards, the plate was rinsed four times with Washing Buffer, 100 μL/well of the mixed samples were added in triplicate and the plate was incubated 3 h at room temperature.

Then, the plate was rinsed three times with Washing Buffer and incubated with Streptavidin Poly-HRP (10 ng/mL in RASA, 100 μL/well) for 1 h at room temperature.

After additional six washes, the plate was incubated with SuperSignal ELISA Femto Maximum Sensitivity Substrate (100 μL/well) for 5 min in the dark and the emitted light was read as counts per second (CPS) with a luminescence plate reader.

TABLE A

| Calibration Curve Preparation | | |
|---|---|---|
| T3S/1 (μL) | T3S/1 Antiserum (μL) | T3S-biotin (μL) |
| CS 5 (1000 pg/mL) 250 | 125 | 50 |
| CS 4 (200 pg/mL) 250 | 125 | 50 |
| CS 3 (40 pg/mL) 250 | 125 | 50 |

TABLE A-continued

Calibration Curve Preparation

|  | T3S/1 (μL) | T3S/1 Antiserum (μL) | T3S-biotin (μL) |
|---|---|---|---|
| CS 2 (8 pg/mL) | 250 | 125 | 50 |
| CS 1 (1.6 pg/mL) | 250 | 125 | 50 |
| B0 | — | 125 | 50 |
| NSB | — | — | 50 |

The calibration curve was prepared in buffer using five concentrations of the test item in the range 1.6-1000 pg/mL. The curve is shown in FIG. 1, panel a).

Example 5

Quantitation of T3S by the Lanthanide Fluorescence Immunoassay

Preparation of Formula V Compound

[[3,5-Diiodo-N-[[(carboxymethyl)[2-[(carboxymethyl)[2-[bis(carboxymethyl)amino]ethyl]amino] ethyl]amino]acetyl]-O-[3-iodo-4-(sulfooxy)phenyl]-L-tyrosinate(6-)]europate(3-)]trisodium (Formula V)

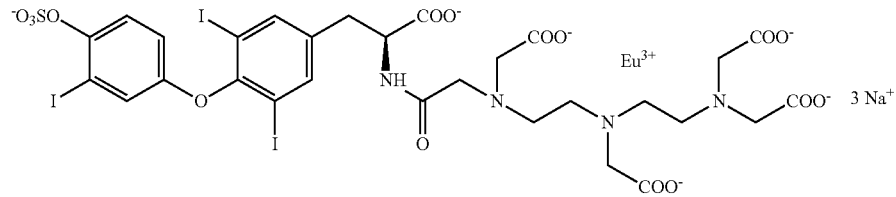

Synthesis of Eu-DTPA-T35 Monoamide

The reaction scheme of the synthesis of 3,5-Diiodo-N-[[(carboxymethyl)[2-[(carboxymethyl)[2-[bis(carboxymethyl)amino]ethyl]amino]ethyl]amino]acetyl]-O-[3-iodo-4-(sulfooxy)phenyl]-L-tyrosine (DTPA-T3S monoamide) is shown in FIG. 2.

A solution of $H_2O$ (0.282 ml; 15.64 mmol) in DMAC (43 mL) was added dropwise to a suspension of N,N-bis[2-(2,6-dioxylenol orange-4-morpholinyl)ethyl]glycine A (4.27 g; 11.94 mmol) in DMAC (85 mL) at room temperature. At the end of the addition the mixture was heated to 80° C. After 4.5 h the reaction mixture was cooled to 25° C. and a solution of T3S/1 (3 g; 3.98 mmol) and DIPEA (2.71 mL; 15.92 mmol) in DMAC (85 mL) was added dropwise over 20 min. DMAC was evaporated under reduced pressure (10 mbar; 40° C.). The oily residue was diluted with $H_2O$ (200 mL), obtaining precipitation of a yellowish solid that was filtered washed with H2O and dried. The crude so obtained was dissolved in Acetone/H2O 20:80 (v/v), the solution (pH=2.97) was loaded on an Amberlite® XAD-1600 resin column (200 mL; diam. 6 cm) and eluted with a Acetone/$H_2O$ gradient. The fractions containing the product having similar composition were collected and evaporated to give the ligand DTPA-T3S as a solid (1.27 g; 1.15 mmol). Yield 26%.

Europium chloride hexahydrate (0.17 g, 0.46 mmol) was added in portions to a solution of the ligand DTPA-T3S (0.51 g; 0.46 mmol) in $H_2O$ (50 mL) at 20° C. (pH 2.93); after each addition the suspension was stirred until complete dissolution. Once the complexation was complete the pH was adjusted to 7 with 0.1 N NaOH and the solution was desalted by elution with water/acetone from a column of Amberlite® XAD-1600 resin (100 mL; diam. 3 cm). The fractions containing the desired product and free from salts were collected and evaporated to give the compound of Formula IV (0.37 g, 0.28 mmol) a yellow solid. Yield: 61%.

The immunoassay method was designed according to: Hemmilä I et al. Anal Biochem. 1984 March; 137(2):335-43. The solutions used were as described in the Example 4 with the following exceptions: a DELFIA® Wash (Perkin Elmer) was used instead of the above Washing buffer. The Tracer stock solution contained the Europium 100 μM and it was stored at +4° C., protected from light. Just before use it was diluted 1:300000 in Assay Buffer to obtain a final concentration of 440 pg/mL.

The assay was performed in DELFIA® Yellow plates (Perkin Elmer).

After the 3-h incubation with the mixed samples, the Formula V diluted compound solution was added (50 μL per well) to all wells. The plates were then sealed with plastic adhesive sheets and incubated under agitation for 1 h at 37° C.

After three washes, the plates were tapped dry on absorbent paper, and Delfia Enhancement Solution (Perkin Elmer) was added (200 μL) After 1 h at 25° C., the plates were read in a Victor3 instrument according to the "Europium" manufacturer protocol.

A calibration curve was prepared using nine concentrations of the test item in the range 30-2000 pg/mL. The curve is shown in FIG. 1, panel b).

Example 6

Synthesis of HRP-T3S monoamide

The conjugate was prepared directly using a commercial kit containing activated HRP (e.g., HOOK™ HRP PLUS Labeling Kit—G-Biosciences). 1-2 mg of T3S was dissolved in 1 mL of the supplied carbonate buffer, then this solution was dispensed in a vial containing the lyophilized activated HRP, mixing gently by repeated pipetting in order to reconstitute the activated enzyme. After about 1 hour at room temperature, 20 μL of the supplied Sodium Cyanoborohydride (NaCNBH3) solution was added, then allowing to react for about 15 min at room temperature. Finally, 50 μL of quenching buffer was added, then incubating with gentle tumbling or shaking for 15 min. The final conjugate was desalted and buffer exchanged in PBS by either dialysis or column desalting. Appropriate dilutions of the T3S-HRP conjugate were prepared and used as a tracer in a single-step ELISA, as described in Example 4, omitting the Streptavidin-HRP incubation step.

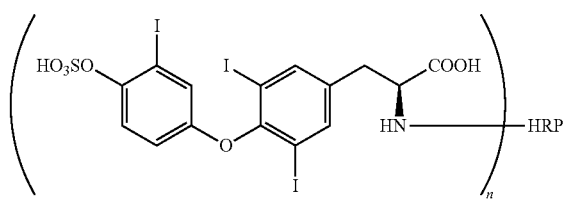

Comparative Example

T3S Synthesis in DMF and Elution Trials

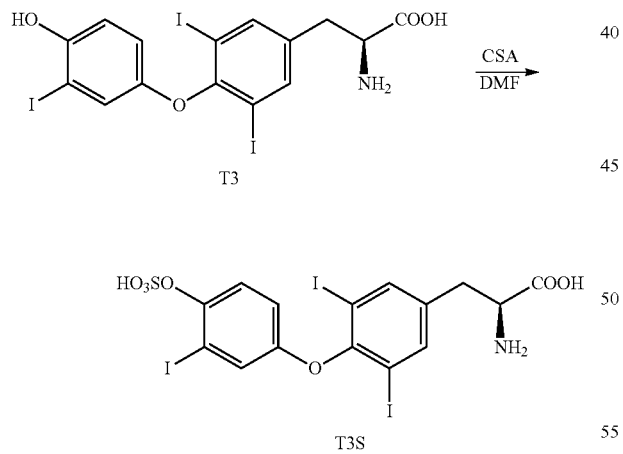

The reaction was carried out according to the scheme above, in DMF.

Briefly: T3 (40 mg) was dissolved in ammoniacal ethanol. This solution was evaporated under a stream of nitrogen.

To the residual, 2 ml of a hot solution of Chlorosulfonic acid (obtained by mixing 2.5 mL of 99% Chlorosulfonic acid and 8 ml of N,N-DMF) was added. Subsequently, the mixture was allowed to reach room temperature under stirring and the reaction was continued overnight.

The mixture was diluted with water (5 mL) and then was eluted on a column of Sephadex LH-20 (5 mL), obtaining fraction A. The elution was continued with 0.1 N HCl (5 mL), obtaining fraction B.

These fractions were re-loaded on column and purified by serial elution of 0.1 N HCl (approx. 4 mL), water and absolute Ethanol.

However, five different water and absolute ethanol quantities were used for purification. The T3S yields and purities obtained by these five conditions have been summarized in Table B.

TABLE B

| | | | Purification trials | | | | |
|---|---|---|---|---|---|---|---|
| | | | T3-Sulfate from aqueous fractions | | | T3-Sulfate from alcoholic fractions | |
| | abs. | | | | | | |
| Trial | H$_2$O (mL) | EtOH (mL) | Amount (mg) | Purity$^{(a)}$ (%) | Yield (%) | Amount (mg) | Purity$^{(a)(b)}$ (%) | Yield$^{(c)}$ (%) |
| 1 | 5 | 10 | 1.0 | 100 | 2.2 | 35 | 80 | 62.3 |
| 2 | 50 | 100 | 2.5 | 100 | 5.6 | 30 | 80 | 53.4 |
| 3 | 125 | 125 | 8.0 | 100 | 17.8 | 30 | 75 | 50.1 |
| 4 | Not registered | 100 | Not registered | Not registered | — | 30 | 75 | 50.1 |
| 5 | 40 | 10 | Not registered | Not registered | — | 10 | 50 | 11.1 |
| | | 20 | Not registered | Not registered | — | 20 | 70 | 31.2 |

$^{(a)}$$^1$H-NMR purity.
$^{(b)}$From the analyses, the product is a mixture of T3S and T3.
$^{(c)}$Yields are calculated on the content of T3-Sulfate.

Table B shows that when the synthesis is carried out in the conditions described above and DMF is used as the solvent, high conversion may be achieved, but the overall yield is quite low.

The invention claimed is:

1. A process for the preparation of a sulfated from of a thyroid hormone having formula II (T$_3$S) according to the following reaction:

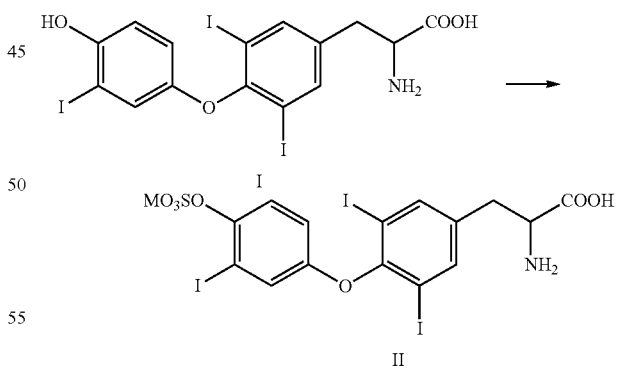

wherein:
M is an alkaline metal;
comprising the steps of:
a) saltation of a compound of formula I with chlorosulfonic acid (CSA) in the presence of dimethylacetamide (DMAC), wherein the molar ratio of CSA to the compound of formula I is from 4 to 10, and wherein more than 90% of the compound of formula I is converted to the sulfated derivative;

b) salification of the sulfated derivative to give a compound of formula II, in an aqueous solution of an alkaline metal inorganic salt; and c) purification of die formula II compound by chromatography on macroreticular aromatic polymeric matrix and elution with a decreasing polarity solution.

2. The process according to claim 1, wherein said inorganic salt is a sodium salt.

3. The process according to claim 1, wherein in step a) the concentration of the compound of formula I in DMAC is from 0.060 to 0.090 mol/L of DMC.

4. The process according to claim 1, wherein the sulfation reaction in step a) is carried out at a temperature below 10° C.

5. The process according to claim 4, wherein the solfation in step a) is left to occur for at least 2 hours.

6. The process according to claim 4, wherein the sulfation reaction step a) is carried out at a temperature from −10° C. to 8° C.

7. The process according to claim 1, wherein the salification according to step b) is carried out in an aqueous solution of $N_aHCO_3$.

8. The process according to claim 1, wherein step c) is preceded by a filtration step.

9. The process according to claim 1, wherein said decreasing polarity solution has a ratio of water to polar solvent from 1.0:0 to 0.7:0.3.

10. The process according to any one of claims 8-9, wherein after elution, the solution is concentrated to at least 10 g of Formula II compound/kg, and the solution is brought to pH values from 5.5 to 6.5.

11. The process according to claim 1, wherein the compound of formula II is obtained as a solid after treatment with an organic polar solvent.

12. The process according to claim 11, wherein said polar organic solvent is selected from the group consisting of: acetone, ethanol, isopropanol and acetonitrile.

13. The process according to claim 11, wherein the compound of formula II in the solid form is further micronized.

14. The process according to an one of claims 11-13, which comprises further admixing the solid and/or micronized form of the compound of formula II, optionally in combination with levo-thyroxine (T4), with at least one diluent selected from the group consisting of: cellulose or a derivative thereof, kaolin, starch and inorganic alkaline salts selected from: calcium and magnesium carbonate.

15. The process according to claim 14, wherein the mixture of the compound of formula II and the diluent which is microcrystalline cellulose, is further admixed with
at least one glidant agent selected from the group consisting of: glycerol dibehenate, tribasic calcium phosphate, talc, starch and starch derivatives, and
at least one disintegerant selected from the group consisting of: croscatmellose or derivatives thereof, crospovidone, polymethylacrylates, maltodextrin, sodium glycolate starch, pre-gelatinized starch, and sodium alginate, and then formulated in tablets by direct compression of the mixture.

16. The process according to clam 15, wherein said mixture is further admixed with at least one lubricating agent selected from the group consisting of: magnesium stearate, zinc stearate, colloidal hydrated silica and collidal silicon dioxide, before being formulated in tablets by direct compression.

17. The process aecording to claim 1, wherein the reagent of formula I is obtained by iodinating a 3',5 di-iodothyronine (T2) with an iodinating agent in an aqueous media and in the presence of an aliphatic amine.

18. The process according to claim 17, wherein the iodinating agent is a mixture comprising $I_2$/NaI.

19. The process according claim 1, wherein M is Na.

20. The process according to claim 1 wherein the molar ratio is from 7 to 9.

* * * * *

UNITED STATES PATENT AND TRADEMARK OFFICE
CERTIFICATE OF CORRECTION

PATENT NO. : 9,890,116 B2
APPLICATION NO. : 14/110237
DATED : February 13, 2018
INVENTOR(S) : Anelli et al.

Page 1 of 1

It is certified that error appears in the above-identified patent and that said Letters Patent is hereby corrected as shown below:

In the Claims

Column 22, Claim 1, Line 39 "a sulfated from" should read – a sulfated form –.
Column 22, Claim 1, step a), Line 62 "saltation" should read – sulfation –.
Column 23, Claim 1, step c), Line 4 "die formula II" should read – the formula II –.
Column 23, Claim 3, Line 11 "DMC" should read – DMAC –.
Column 23, Claim 5, Line 16 "solfation" should read – sulfation –.
Column 24, Claim 14, Line 4 "an one of" should read – any one of –.
Column 24, Claim 15, Line 18 "croscatmellose" should read – croscarmellose –.
Column 24, Claim 16, Line 23 "clam 15" should read – claim 15 –.
Column 24, Claim 16, Line 26 "collidal" should read – colloidal –.
Column 24, Claim 17, Line 29 "aecording to" should read – according to –.
Column 24, Claim 19, Line 35 "according claim 1" should read – according to claim 1 –.

Signed and Sealed this
Sixteenth Day of April, 2019

Andrei Iancu
*Director of the United States Patent and Trademark Office*